(12) United States Patent
Kim et al.

(10) Patent No.: US 8,402,839 B2
(45) Date of Patent: Mar. 26, 2013

(54) JIG FOR COMPRESSION TEST IN A HEATING FURNACE

(75) Inventors: Hyung Jun Kim, Gyeonggi-do (KR); Heung Youl Kim, Seoul (KR)

(73) Assignee: Korea Institute of Construction Technology, Gyeonggi-Do (KR)

( * ) Notice: Subject to any disclaimer, the term of this patent is extended or adjusted under 35 U.S.C. 154(b) by 257 days.

(21) Appl. No.: 12/941,264

(22) Filed: Nov. 8, 2010

(65) Prior Publication Data

US 2011/0107854 A1    May 12, 2011

(30) Foreign Application Priority Data

Nov. 10, 2009    (KR) .................. 10-2009-0108280

(51) Int. Cl.
*G01N 3/02*    (2006.01)
(52) U.S. Cl. ........................................................ 73/856
(58) Field of Classification Search .................... 73/856
See application file for complete search history.

(56) References Cited

U.S. PATENT DOCUMENTS

| | | | |
|---|---|---|---|
| 2,705,431 A * | 4/1955 | Angelo | 408/97 |
| 4,490,111 A | 12/1984 | Yakura | |
| 5,948,994 A * | 9/1999 | Jen et al. | 73/856 |
| 7,407,378 B2 * | 8/2008 | Brum | 425/515 |
| 2004/0253065 A1* | 12/2004 | Davis | 408/115 R |

OTHER PUBLICATIONS

Louise Crocker et al, "Measurement Methods for Obtaining Volumetric Coefficients for Hyperelastic Modelling of Flexible Adhesives", Project PAJex2-Flexible Adhesives, PAJex2 Report No. 3, issued on Jan. 2001, p. 1-p. 21.

* cited by examiner

*Primary Examiner* — Lisa Caputo
*Assistant Examiner* — Octavia D. Hollington
(74) *Attorney, Agent, or Firm* — J.C. Patents (57) ABSTRACT

Provided is a jig for a compression test in a heating furnace capable of variously changing boundary conditions such as a both-end hinge, a both-end fixing, or one-end hinge and one-end fixing through simple attachment and detachment of a holder. Therefore, it is possible to easily implement hinge and fixing conditions of a test sample installed in a heating furnace using one jig, remarkably reducing time and cost consumed to install the test sample.

5 Claims, 6 Drawing Sheets

JIG FOR COMPRESSION TEST IN A HEATING FURNACE

CROSS-REFERENCE TO RELATED APPLICATION

This application claims the priority benefits of Korea patent application serial no. 10-2009-0108280, filed on Nov. 10, 2009. The entirety of the above-mentioned patent applications is hereby incorporated by reference herein and made a part of specification.

BACKGROUND

1. Field

The present invention relates to a jig for a compression test in a heating furnace installed in the heating furnace to implement boundary conditions, and more particularly, to a jig for a compression test in a heating furnace in which a set of jigs are installed at upper and lower ends of a test sample to variously change boundary conditions such as a both-end hinge, a both-end fixing, or a one-end hinge and one-end fixing through simple attachment/detachment of a holder, remarkably reducing time and cost consumed to install the test sample.

2. Description of the Related Art

In general, when a building is on fire, a structural member constituting the building is exposed to a large amount of heat and is structurally weakened, making it unable to maintain its structural strength. Accordingly, when the building is on fire, the strength of the structure is decreased, causing the building to easily collapse, which frequently results in serious casualties.

Since use performance limits or structural destruction of the structural member affected by the large amount of heat upon fire of the building structure are determined according to support conditions, load states and fire-exposed surfaces as well as physical and thermal characteristics of a material constituting the building structure, it is important to perform fire-resistance design of the structure in consideration of this.

With regard to the above, the structural member is installed in a heating furnace and heat is applied to the structural member to perform a strength test so that actual fire tests and various performance test of the structural member are essentially needed.

Figure 1A:
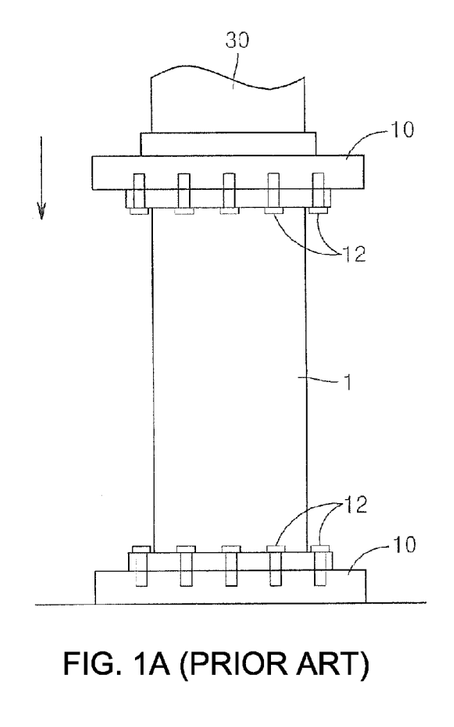
FIG. 1A is a view for explaining a conventional method of implementing an end fixing condition.
Figure 1B:
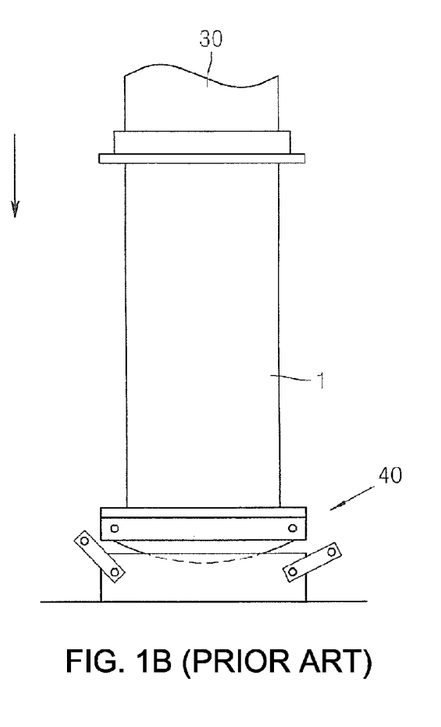
FIG. 1B is a view for explaining a conventional method of implementing a hinge condition.

FIGS. 1A and 1B show end fixing conditions of a test sample according to a prior art. When the test sample is in a heating test, the end fixed state can be confirmed by checking whether moment occurs from an end of the test sample according to application of a load, or measuring rotation and movement of the end of the test sample.

A typical method of implementing end fixing conditions, as shown in FIG. 1A, is performed by fixing an end of a test sample 1 to a frame 10 using bolts 12, etc., and applying a load to fix the end of the test sample 1 using a clamp 30 of a load tester. It will be appreciated that, in the end fixing conditions, both ends of the test sample 1 are fastened to the frame 10 using the bolts 12 so that rotation or deformation of the test sample 1 is restricted.

FIG. 1B shows a hinge jig 40 having a projected hemispherical shape used in a conventional compression test. In most cases, since a force application part of the load tester has a jaw shape to protect a cylinder as an actuator, the hinge jig 40 is installed at only a lower end of the test sample 1.

When the conventional hinge jig 40 is mounted and a force is applied using the clamp 30 of the load tester, provided that upper and lower ends of the test sample are hinged, even when the end of the test sample 1 is rotated to generate bending or buckling thereof, it is possible to prevent generation of moment from the end of the test sample 1.

However, the conventional jigs for a compression test have problems in that only simple fixing or hinge boundary conditions can be implemented. Therefore, different types of various jigs must be prepared according to test conditions at every time, and time and cost consumed to install the test sample are largely increased.

SUMMARY

In order to solve the problems of the conventional jig in that only simple fixing or hinge boundary conditions can be implemented, the present invention relates to a jig for a compression test in a heating furnace capable of easily implementing hinge and fixing conditions using one jig to variously change boundary conditions, remarkably reducing time and cost consumed to install a test sample.

According to an exemplary aspect, there is provided a jig for a compression test in a heating furnace used in a force application test of a test sample, which includes: an upper plate having an upper surface in which concave fixing grooves are formed in edges thereof, and a lower surface in which a hemispherical projection is formed at a center thereof; a lower plate correspondingly disposed under the upper plate, and having a lower surface in which fixing grooves are formed in edges thereof to correspond to the fixing grooves of the upper surface of the upper plate and an upper surface in which a hemispherical concave part is formed to correspond to the hemispherical projection of the upper plate so that the upper plate is seated thereon; and holders each having an upper flange inserted into the fixing groove of the upper surface of the upper plate, a lower flange inserted into the fixing groove of the lower surface of the lower plate, and a middle flange inserted into a gap between the upper plate and the lower plate, which project from one surface thereof, to prevent rotation or movement of the upper and lower plates and, wherein a hinge condition and an end fixing condition of a test sample are implemented through attachment and detachment of the holders. Therefore, it is possible to easily implement hinge and fixing conditions of a test sample installed in a heating furnace using one jig, remarkably reducing time and cost consumed to install the test sample.

In addition, the jig for a compression test in a heating furnace may further include an upper flat fastening plate on the upper plate, wherein the upper plate is coupled to the upper plate by bolts and then disposed between clamps of a load tester to structurally reinforce the upper plate.

Further, the jig for a compression test in a heating furnace may further include a force application plate disposed under the lower plate and installed in a heating furnace, wherein fixing pins project from the lower surface of the lower plate to be inserted into holes of the force application plate to prevent movement thereof Furthermore, the upper plate and the lower plate may have a parallelepiped structure having right-angled corners, and the fixing grooves and of the upper plate and the lower plate may be formed in plural in the right-angled corners thereof, respectively, so that the holders are mounted in the right-angled corners. Therefore, it is possible to stably fix the upper plate and the lower plate to perform a compression test.

In addition, the holders may further include bolt holes formed to pass through bodies thereof in a lateral direction, and bolts coupled to the bolt holes, and, in a state in which the holders may be coupled to the upper plate and the lower plate, the bolts may be threaddedly engaged with the bolt holes so that ends of the bolts push side surfaces of the upper plate and the lower plate to separate the holders from the fixing grooves and of the upper plate and the lower plate.

BRIEF DESCRIPTION OF THE DRAWINGS

The accompanying drawings, which are included to provide a further understanding of the invention and are incorporated in and constitute a part of this specification, illustrate exemplary embodiments of the invention, and together with the description serve to explain the aspects of the invention.

DETAILED DESCRIPTION

The invention is described more fully hereinafter with reference to the accompanying drawings, in which exemplary embodiments of the invention are shown. This invention may, however, be embodied in many different forms and should not be construed as limited to the exemplary embodiments set forth herein. Rather, these exemplary embodiments are provided so that this disclosure is thorough, and will fully convey the scope of the invention to those skilled in the art.

Figure 2:
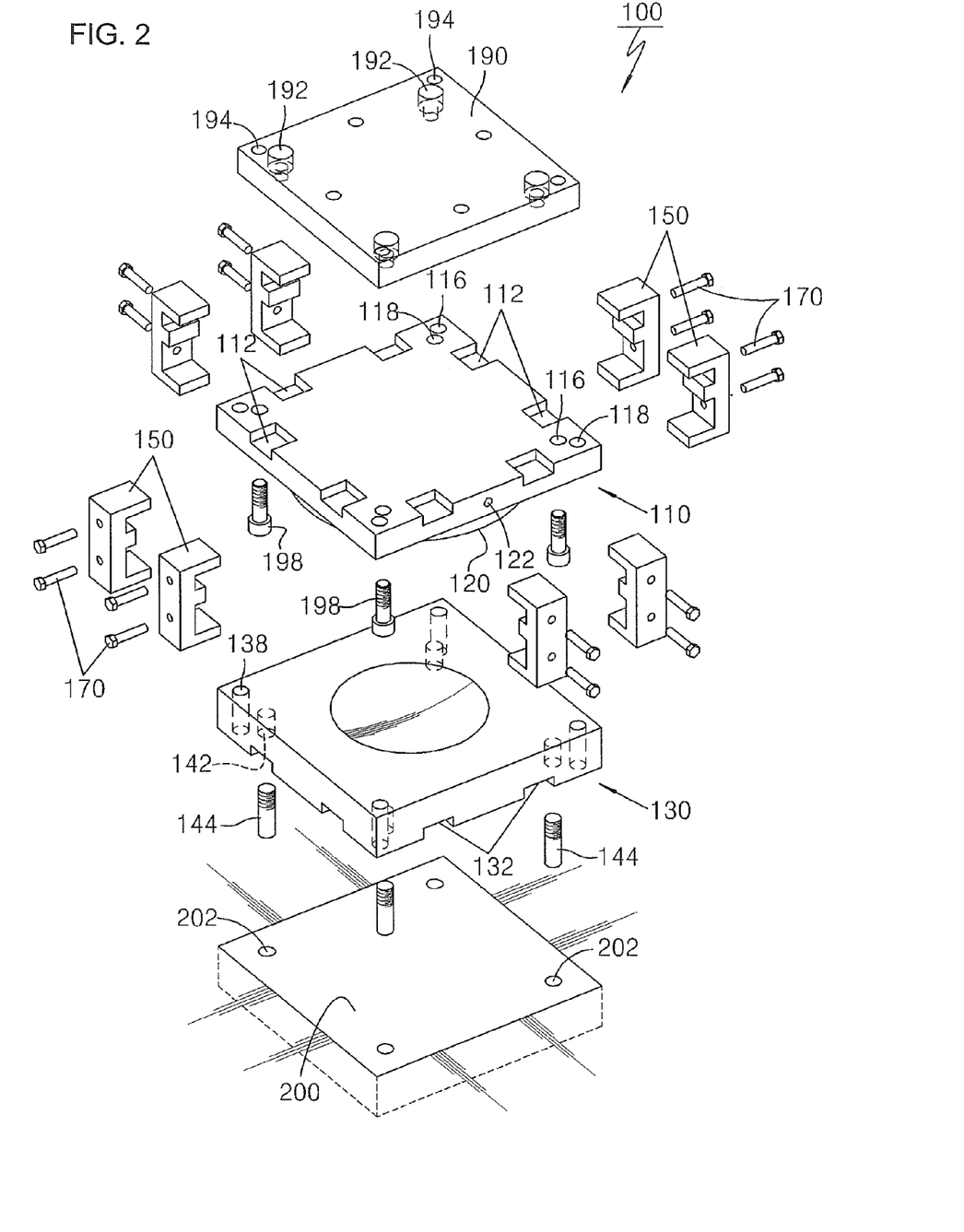
FIG. 2 is an exploded perspective view of a jig for a compression test in a heating furnace in accordance with the present invention.

As shown in FIG. 2, a jig 100 for a compression test in a heating furnace in accordance with the present invention includes an upper plate 110, a lower plate 130 and holders 150, which are used in a force application test.

Figure 3A:
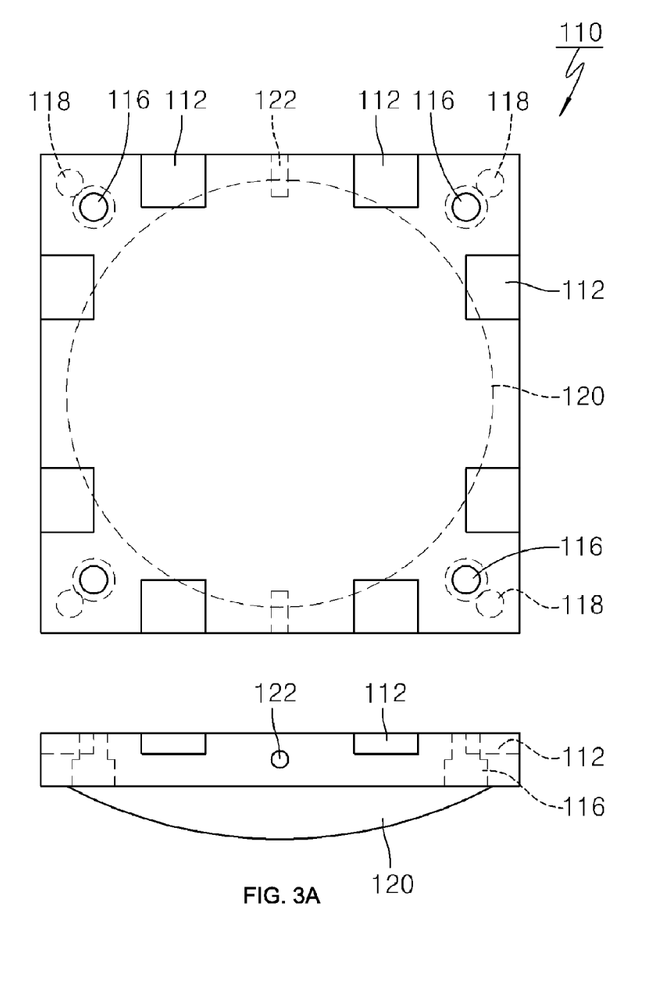
FIG. 3A shows a plan view and a side view of an upper plate provided in the jig for a compression test in a heating furnace in accordance with the present invention.

As shown in FIG. 3A, in the jig 100 for a compression test in a heating furnace in accordance with the present invention, the upper plate 110 includes fixing grooves 112 formed in edges of an upper surface thereof, and a hemispherical projection 120 projecting downward from a center of a lower surface thereof.

The upper plate 110 may have a parallelepiped structure having right-angled corners, and the fixing grooves 112 are formed in plural around the right-angled corners. The upper plate 110 is configured such that the hemispherical projection 120 formed at the lower surface corresponds to an apex disposed at a center of the upper plate 110.

In addition, the upper plate 110 has a plurality of bolt holes formed in the four corners. The bolt holes include bolt holes 116 to which the upper fastening plate is coupled, and bolt holes 118 to which a test sample is coupled. Further, female-threaded holes 122 are formed in both side surfaces of the upper plate 110 to install central rings, respectively.

Figure 3B:
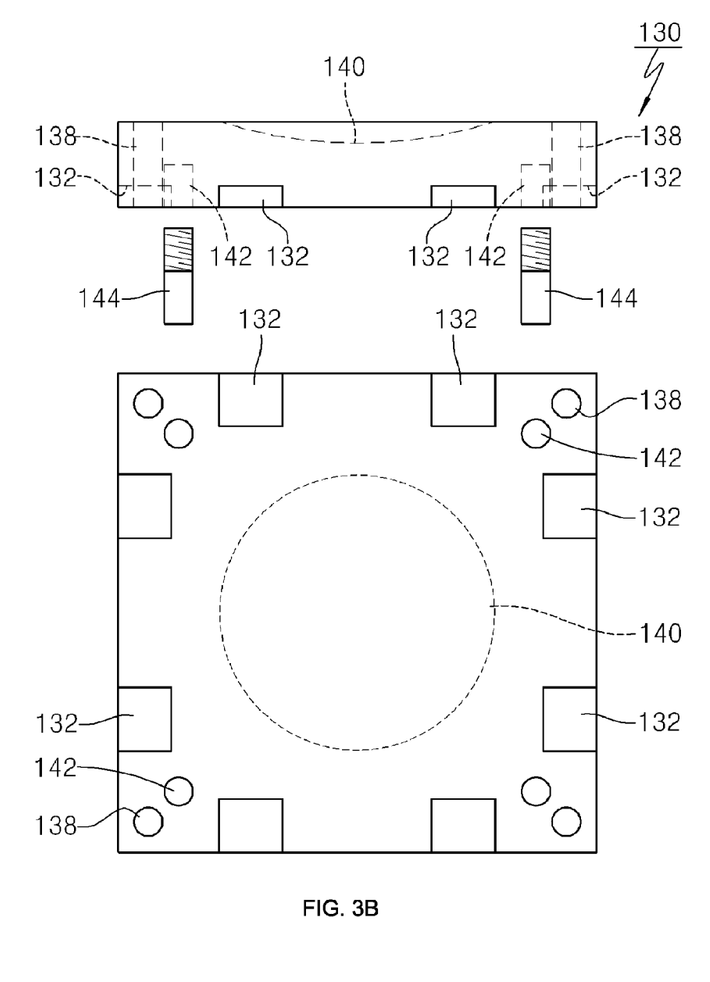
FIG. 3B shows a side view and a bottom view of a lower plate provided in the jig for a compression test in a heating furnace in accordance with the present invention.

Further, the jig 100 for a compression test in a heating furnace in accordance with the present invention includes the lower plate 130 corresponding to the upper plate 110 and disposed under the upper plate 110.

The lower plate 130 has fixing grooves 132 formed at edges of a lower surface thereof and corresponding to the fixing grooves 112 of the upper surface of the upper plate 110, and a hemispherical concave part 140 formed at an upper surface thereof and corresponding to the hemispherical projection 120 of the upper plate 110 so that the upper plate 110 is seated thereon.

The lower plate 130 may have a parallelepiped structure having right-angled corners corresponding to the upper plate 110, and the fixing grooves 132 are formed in plural around the right-angled corners.

In addition, the lower plate 130 has bolt holes 138 formed around four corners and to which a test sample is coupled, and pin holes 142 formed around four corners of the lower surface and to which a force application plate 200 to be described below is coupled. Fixing pins 144 are inserted into the pin holes 142, respectively.

Figure 4A:
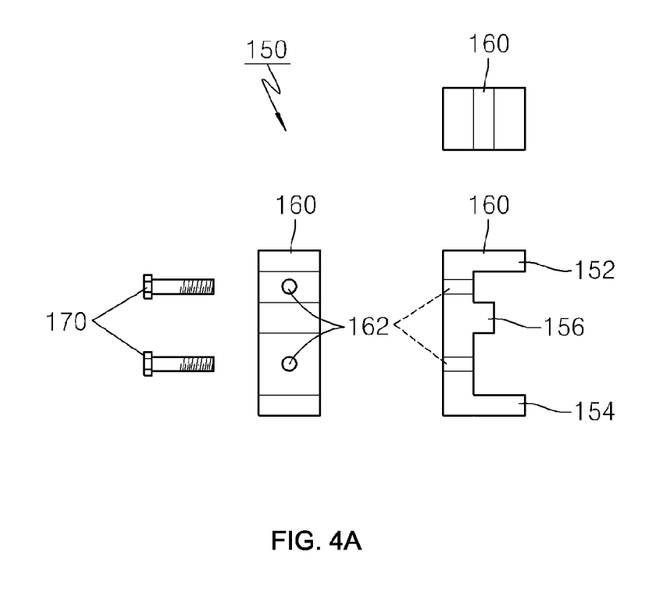
FIG. 4A shows a plan view and left and right side views of a holder provided in the jig for a compression test in a heating furnace in accordance with the present invention.

Further, as shown in FIG. 4A, the jig 10 for a compression test in a heating furnace in accordance with the present invention includes the holders 150 to prevent rotation or movement between the upper plate 110 and the lower plate 130.

Each of the holders 150, which has an E-shaped cross-section, includes an upper flange 152 inserted into the fixing groove 112 of the upper surface of the upper plate 110, a lower flange 154 inserted into the fixing groove 132 of the lower surface of the lower plate 130, and a middle flange 156 inserted into a gap between the upper plate 110 and the lower plate 130, which project from one surface of a body 160 of the holder 150.

In addition, the body 160 has bolt holes 162 formed to pass through the body in a lateral direction, and bolts 170 are used to separate the holder 150 fixed to the upper plate 110 and the lower plate 130 from the upper plate 110 and the lower plate 130. That is, in a state in which the holder 150 is inserted into the upper plate 110 and the lower plate 130 to be integrally fixed thereto, when the bolts 170 are threaddedly engaged with the bolt holes 162 of the body 160, ends of the bolts 170 push the side surfaces of the upper plate 110 and the lower plate 130 to separate the holder 150 from the fixing grooves 112 and 132 of the upper plate 110 and the lower plate 130.

Figure 4B:
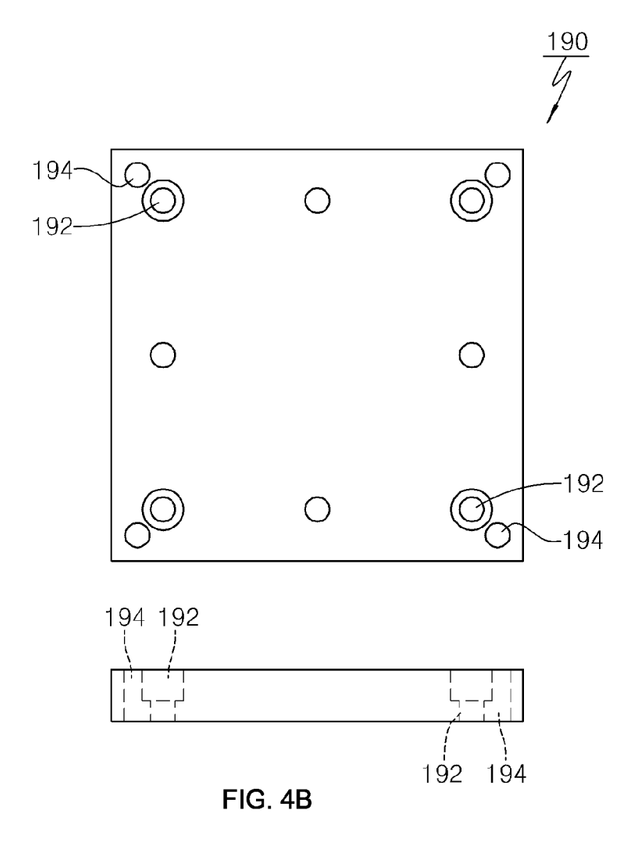
FIG. 4B shows a plan view and a side view of an upper fastening plate provided in the jig for a compression test in a heating furnace in accordance with the present invention.

Further, as shown in FIG. 4B, the jig 100 for a compression test in a heating furnace in accordance with the present invention further includes an upper flat fastening plate 190 disposed on the upper plate 110.

The upper fastening plate 190 has bolt holes 192 to which the upper plate is coupled, and bolt holes 194 to which a test sample is coupled, which are formed at four corners. When an actual compression load test is performed, the upper fastening plate 190 is coupled to the upper plate 110 by bolts 198, and then, disposed between clamps of the load tester to structurally reinforce the upper plate 110.

In addition, the jig 100 for a compression test in a heating furnace in accordance with the present invention further includes a force application plate 200 disposed under the lower plate 130 and installed in a heating furnace. The force application plate 200 is fixed to a bottom surface of the heating furnace, and has holes 202 corresponding to the pin holes 142 of the lower plate 130 so that the fixing pins 144 projecting from the lower surface of the lower plate 130 are inserted to prevent movement of the lower plate 130 during the compression test.

Figure 5A:
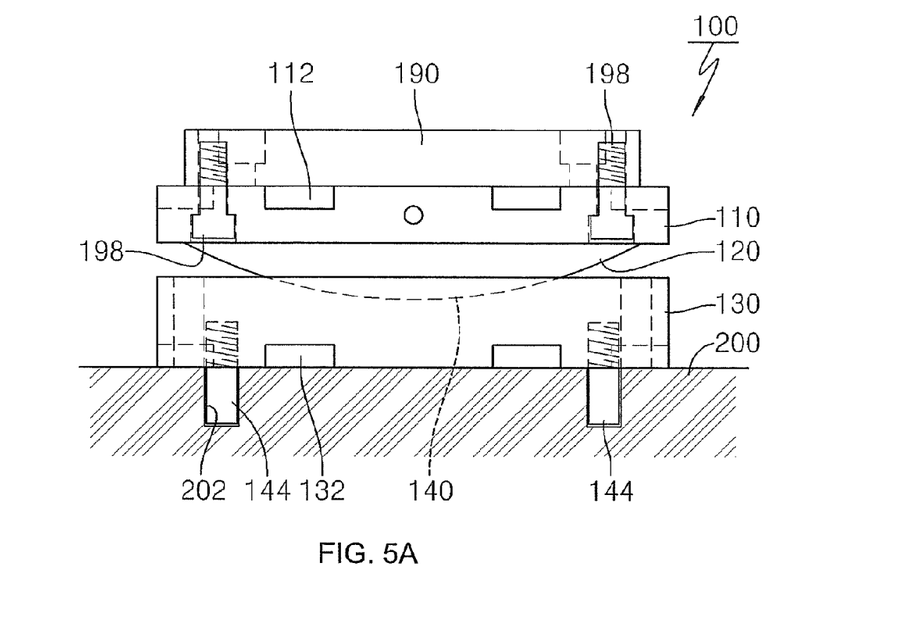
FIG. 5A is a cross-sectional view of the jig for a compression test in a heating furnace in accordance with the present invention assembled in a hinge condition.

As shown in FIG. 5A, in the jig 100 for a compression test in a heating furnace in accordance with the present invention, when the hinge condition is implemented, the holders 150 are removed, the hemispherical projection 120 formed at the lower surface of the upper plate 110 is disposed to align with the hemispherical concave part 140 formed in the upper surface of the lower plate 130, and a test sample is installed to receive a load. In this case, as the test sample is deformed due to rotation the upper plate 110 and the lower plate 130 may be rotated with respect to each other to release a degree of freedom of an end of the test sample.

Figure 5B:
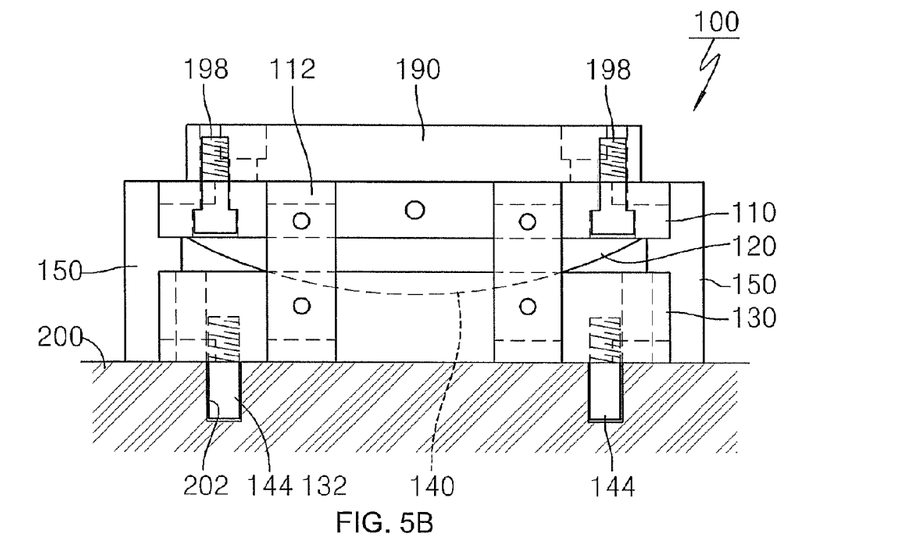
FIG. 5B is a cross-sectional view of the jig for a compression test in a heating furnace in accordance with the present invention assembled in an end fixing condition.

However, when the end fixing condition is needed, as shown in FIG. 5B, the holders 150 are installed to prevent rotation of the upper plate 110 and the lower plate 130 and prevent rotation or movement of the end of the test sample, implementing the end fixing condition.

In the end fixing condition, the upper flanges 152 of the holders 150 are inserted into the fixing grooves 112 of the upper surface of the upper plate 110, the lower flanges 154 are inserted into the fixing grooves 132 of the lower surface of the lower plate 130, and the middle flanges 156 are inserted into the gap between the upper plate 110 and the lower plate 130 to fix the upper and lower plates 110 and 130. Accordingly, it is possible for the jig 100 for a compression test in a heating furnace in accordance with the present invention to implement the end fixing condition using the holders 150.

Hereinafter, a method of installing a jig 100 for a compression test in a heating furnace in accordance with the present invention and implementing a boundary condition such as a both-end hinge, a both-end fixing, or a one-end hinge and one-end fixing will be described.

In implementing the boundary condition using the jig 100 for a compression test in a heating furnace in accordance with the present invention, two jigs 100 for a compression test in a heating furnace in accordance with the present invention are installed at upper and lower parts of a test sample S in the heating furnace. The jig 100 installed at the upper part of the test sample S is fixed by fastening the upper fastening plate 190 and the upper plate 110 using the bolts 198, and the lower plate 110 is fixed to the test sample S using bolts 210.

Next, the jig 100 installed at the lower part of the test sample S is installed by inserting the fixing pins 144 for preventing movement of the lower part into the holes 202 formed in the force application plate 200 and fixing the lower plate 130, and the upper plate 110 is fixed to the test sample S using the bolts 220.

As described above, after installing the two jigs at the upper and lower parts of the test sample S, respectively, a clamp 230 of a force application tester is disposed on the upper fastening plate 190 to perform a force application test.

Figure 6A:
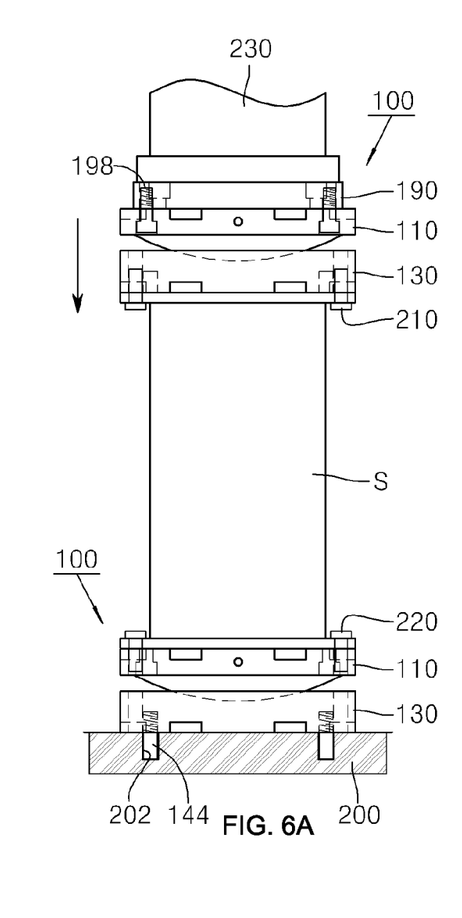
FIG. 6A is a cross-sectional view in which a test sample is fixed in a boundary condition of both-end hinge using the jig for a compression test in a heating furnace in accordance with the present invention.

Meanwhile, in order to perform the force application test, as shown in FIG. 6A, after installing the test sample S and the jigs 100, the holders 150 are removed, implementing the both-end hinge boundary condition using the jigs 100 for a compression test in a heating furnace in accordance with the present invention.

At this time, when removal of the holders 150 is needed, the bolts 170 are inserted into the bolt holes 162 formed in the bodies 160 of the holders 160. When the bolts 170 are rotated, ends of the bolts 170 push the side surfaces of the upper plate 110 and the lower plate 130 to remove the holders 150 from the upper plate 110 and the lower plates 130.

Figure 6B:
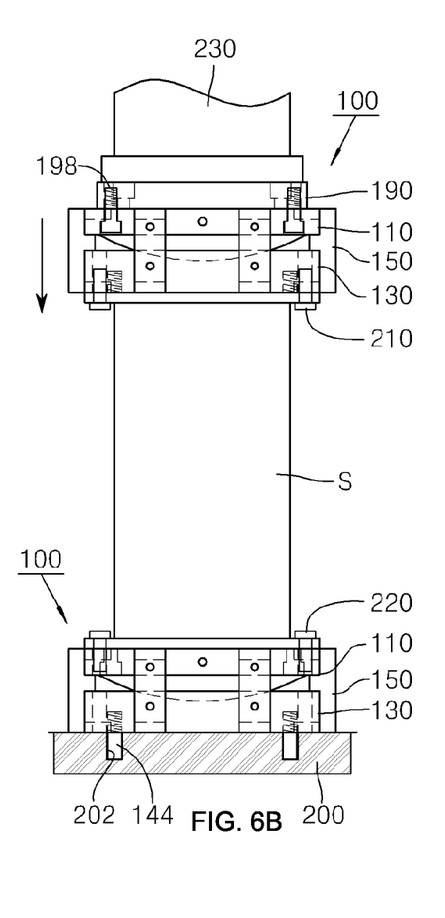
FIG. 6B is a cross-sectional view in which a test sample is fixed in a boundary condition of a both-end fixing state using the jig for a compression test in a heating furnace in accordance with the present invention.

In addition, as shown in FIG. 6B, the jigs 100 for a compression test in a heating furnace in accordance with the present invention are installed to implement the both-end fixing boundary condition through the following method.

First, the upper plate 110 is parallelly disposed on the lower plate 130. Next, the holders 150 are inserted into the fixing grooves 112 and 132 formed in the upper plate 110 and the lower plate 130. Since the holders 150 are manufactured to have a tolerance of, for example, 4/100, the holders 150 must be press-fitted into the fixing grooves 112 using a rubber hammer, etc., to prevent the holders 150 and the fixing grooves 112 from being damaged due to excessive forces or impacts.

In addition, when the holders 150 are removed, the bolts 170 are inserted into the bolt holes 62 formed in the side surfaces of the holders 150 to space the holders 150 from the upper plate 110 and the lower plate 130. When the holders 150 are spaced apart from the upper plate 110 and the lower plate 130 using the bolts 170, a worker must carefully operate such that the bolts 170 can remove the holders 150 from the upper plate 110 and the lower plate 130 without deformation.

Figure 6C:
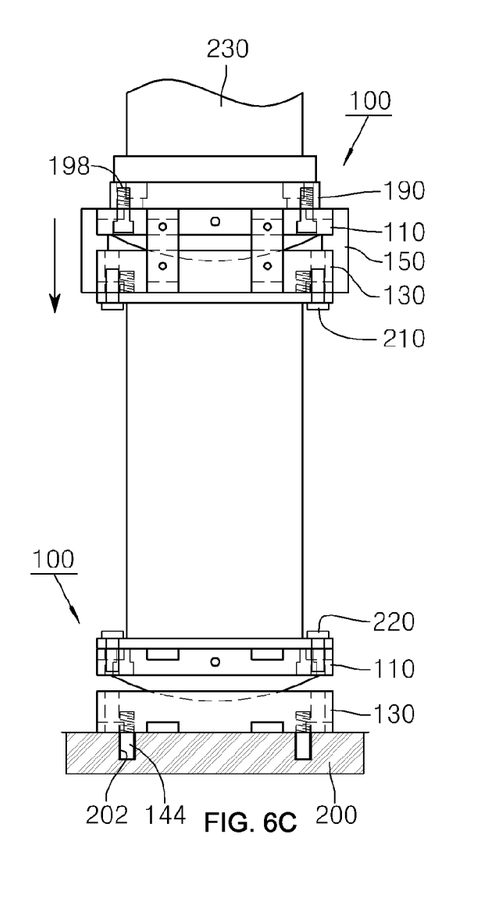
FIG. 6C is a cross-sectional view in which a test sample is fixed in a boundary condition of one-end hinge and a one-end fixing state using the jig for a compression test in a heating furnace in accordance with the present invention.

Further, as shown in FIG. 6C, the one-end hinge and one-end fixing boundary condition can be implemented using the jigs 100 for a compression test in a heating furnace in accordance with the present invention.

As apparent from the above description, the jig for a compression test in a heating furnace in accordance with the present invention can easily implement a hinge condition and a fixing condition of the test sample installed in the heating furnace using one jig, variously changing boundary conditions and remarkably reducing time and cost consumed to install the test sample.

It will be apparent to those skilled in the art that various modifications and variations can be made in the present invention without departing from the spirit or scope of the invention. Thus, it is intended that the present invention covers the modifications and variations of this invention provided they come within the scope of the appended claims and their equivalents.

What is claimed is:

1. A jig for a compression test in a heating furnace used in a force application test of a test sample, which comprises:
   an upper plate (110) having an upper surface in which concave fixing grooves (112) are formed in edges thereof, and a lower surface in which a hemispherical projection (120) is formed at a center thereof;
   a lower plate (130) correspondingly disposed under the upper plate (110), and having a lower surface in which fixing grooves (132) are formed in edges thereof to correspond to the fixing grooves (112) of the upper surface of the upper plate (110) and an upper surface in which a hemispherical concave part (140) is formed to correspond to the hemispherical projection (120) of the upper plate (110) so that the upper plate (110) is seated thereon; and
   holders (150) each having an upper flange (152) inserted into the fixing groove (112) of the upper surface of the upper plate (110), a lower flange (154) inserted into the fixing groove (132) of the lower surface of the lower plate (130), and a middle flange (156) inserted into a gap between the upper plate (110) and the lower plate (130), which project from one surface thereof, to prevent rotation or movement of the upper and lower plates (110) and (130), wherein a hinge condition and an end fixing condition of a test sample (S) are implemented through attachment and detachment of the holders (150).

2. The jig for a compression test in a heating furnace according to claim 1, further comprising an upper flat fastening plate (190) on the upper plate (110), wherein the upper plate (190) is coupled to the upper plate (110) by bolts (198) and then disposed between clamps (230) of a load tester to structurally reinforce the upper plate (110).

3. The jig for a compression test in a heating furnace according to claim 1, further comprising a force application plate (200) disposed under the lower plate (130) and installed in a heating furnace, wherein fixing pins (144) project from the lower surface of the lower plate (130) to be inserted into holes (202) of the force application plate (200) to prevent movement thereof.

4. The jig for a compression test in a heating furnace according to any one of claims 1 to 3, wherein the upper plate (110) and the lower plate (130) have a parallelepiped structure having right-angled corners, and the fixing grooves (112) and (132) of the upper plate (110) and the lower plate (130) are formed in plural in the right-angled corners thereof, respectively, so that the holders (150) are mounted in the right-angled corners.

5. The jig for a compression test in a heating furnace according to claim 4, wherein the holders (150) further comprise bolt holes (162) formed to pass through bodies (150) thereof in a lateral direction, and bolts (170) coupled to the bolt holes (162), and, in a state in which the holders (150) are coupled to the upper plate (110) and the lower plate (130), the bolts (170) are threadedly engaged with the bolt holes (162) so that ends of the bolts (170) push side surfaces of the upper plate (110) and the lower plate (130) to separate the holders (150) from the fixing grooves (112) and (132) of the upper plate (110) and the lower plate (130).

* * * * *